United States Patent
Mikhail (10) Patent No.: US 9,265,667 B2
(45) Date of Patent: Feb. 23, 2016

(54) BIODEGRADABLE WATER SOLUBLE TAMPON APPLICATOR AND PROCESS AND APPARATUS TO MANUFACTURE SAME

(75) Inventor: John Mikhail, Tecumseh (CA)

(73) Assignees: Louis Thomas Mikhail, Windsor (CA); Joseph Bakhus Mikhail, Windsor (CA)

( * ) Notice: Subject to any disclaimer, the term of this patent is extended or adjusted under 35 U.S.C. 154(b) by 142 days.

(21) Appl. No.: 13/978,285

(22) PCT Filed: Jan. 6, 2012

(86) PCT No.: PCT/CA2012/000015
§ 371 (c)(1),
(2), (4) Date: Jul. 3, 2013

(87) PCT Pub. No.: WO2012/092671
PCT Pub. Date: Jul. 12, 2012

(65) Prior Publication Data
US 2013/0281912 A1      Oct. 24, 2013

Related U.S. Application Data

(60) Provisional application No. 61/430,711, filed on Jan. 7, 2011.

(51) Int. Cl.
*A61F 13/32* (2006.01)
*A61F 13/26* (2006.01)
(Continued)

(52) U.S. Cl.
CPC ....... *A61F 13/2097* (2013.01); *A61F 13/15252* (2013.01); *A61F 13/2082* (2013.01); *A61F 13/266* (2013.01)

(58) Field of Classification Search
CPC .................................................. A61F 13/266
See application file for complete search history.

(56) References Cited

U.S. PATENT DOCUMENTS 2,526,683 A    10/1950   Murphy
4,508,531 A     4/1985   Whitehead
(Continued)

FOREIGN PATENT DOCUMENTS

EP    0104039 A1   3/1984
WO    0015165 A1   3/2000
(Continued)

OTHER PUBLICATIONS

Written Opinion and International Search Report from International Patent Application No. PCT/CA2012/000015.

*Primary Examiner* — Susan Su
(74) *Attorney, Agent, or Firm* — Eric L. Lane; Green Patent Law (57) ABSTRACT

A substantially biodegradable and water soluble tampon applicator comprising: a plunger and a barrel, said plunger being of a predetermined length, and having a first end and a second end, said second end being a predetermined distance from said first end, said plunger being substantially cylindrical in shape and having a first diameter at said first end and a second diameter at said second end, wherein said first diameter tapers downwards to said second diameter, proximate said first end, said plunger further comprises a first mating portion, said barrel having a first end and a second end, said second end being a predetermined distance from said first end, said barrel being substantially cylindrical in shape and having a diameter greater than the first diameter of said plunger, proximate said first end of said barrel, there is provided a second mating portion to matingly engage said first mating portion of said plunger to maintain said plunger in relation to said barrel in a first position, proximate said first end of said barrel, adjacent said second mating portion, said barrel further comprises a fingergrip.

19 Claims, 7 Drawing Sheets

(51) Int. Cl.
*A61F 13/20* (2006.01)
*A61F 13/15* (2006.01)

(56) References Cited

U.S. PATENT DOCUMENTS

| | | | |
|---|---|---|---|
| 4,667,498 A | 5/1987 | Sauter | |
| 4,846,802 A * | 7/1989 | Sanders, III | 604/15 |
| 5,350,354 A * | 9/1994 | Billmers | A61F 13/26 604/11 |
| 5,693,009 A * | 12/1997 | Fox | A61F 13/26 604/14 |
| 2004/0054317 A1* | 3/2004 | Lemay et al. | 604/15 |
| 2006/0004320 A1* | 1/2006 | Berg et al. | 604/15 |
| 2006/0173400 A1* | 8/2006 | Suga et al. | 604/18 |
| 2007/0161942 A1 | 7/2007 | Cirovski et al. | |
| 2007/0214973 A1* | 9/2007 | Hook et al. | 101/6 |
| 2007/0276317 A1* | 11/2007 | Henderson et al. | 604/15 |
| 2008/0154176 A1* | 6/2008 | Van Ingelgem et al. | 604/18 |
| 2009/0247930 A1* | 10/2009 | Fung | 604/16 |
| 2010/0016780 A1* | 1/2010 | VanDenBogart et al. | 604/15 |
| 2010/1618410 | 7/2010 | Cade et al. | |
| 2010/0324468 A1* | 12/2010 | Gann et al. | 604/15 |
| 2011/0273727 A1* | 11/2011 | Seki et al. | 356/634 |

FOREIGN PATENT DOCUMENTS

| | | |
|---|---|---|
| WO | 2005018520 A1 | 3/2005 |
| WO | 2006005008 A1 | 1/2006 |

* cited by examiner

BIODEGRADABLE WATER SOLUBLE TAMPON APPLICATOR AND PROCESS AND APPARATUS TO MANUFACTURE SAME

FIELD OF INVENTION

The present invention relates to a biodegradable water soluble tampon applicator and processes and apparatus to manufacture same.

BACKGROUND OF THE INVENTION

There is a large environmental concern surrounding Feminine Hygiene products. A woman uses about 16,800 tampons or sanitary pads in her lifetime. Waste consultant Franklin Associates reports that 6.5 billion tampons end up in landfills or sewage systems in the USA. About 2.5 million tampons, 1.4 million pads & 700,000 panty liners were flushed away daily.

Tampon Applicators in current commercial use are typically made from either an insoluble plastic or a flushable smooth surfaced cardboard. Plastic tampon applicators are preferred by women but are typically made of insoluble polyethylene using an injection-molding process. These plastic tampon applicators have always posed and still pose a significant environmental and aesthetic problem as they continue to be flushed down toilets in alarming numbers instead of being disposed of with the dry trash. This is a continued annoyance as plastic tampon applicators also have a tendency to wash up on local beaches and wreak havoc on municipal treatment plants.

Although cardboard is considered to be more environmentally friendly compared to plastic, it still requires up to 6 months to fully dissolve when disposed of in a toilet.

Furthermore, cardboard applicators are less popular among females due primarily to the insertion difficulties that are associated with cardboard applicators. These difficulties range from the lack of strong grip rings to inferior slip characteristics and lack of comfortable petal shaped or conical shaped tips.

Cardboard tampon applicators can also be more difficult to shape and more difficult to make smooth cuts (i.e. petal cuts) that will not cause issues on insertion, such as inconvenience and lack of comfort.

Cardboard tampon applicators are commonly thought of as less comfortable to insert and are more difficult to form into shapes other than uniform cylindrical tubes.

Many cardboard tampon applicators are coated with a non-compostable coating to strengthen the applicator and/or reduce the coefficient of friction rendering the tampon applicator less environmentally friendly.

Furthermore, cardboard tampon applicators tend to collect grease as they travel through the wastewater system causing serious problems with grease balls.

The gripping structures on cardboard tampon applicators are typically formed after the cardboard has been formed into tube-like shapes. This results in an added processing step, which translates to increased cost.

Currently there is no type of indicia, such as branding, logos, or a message on the tampon applicator, available in the market place.

It is therefore an object of the invention to provide a biodegradable tampon applicator which is environmentally friendly and substantially water soluble.

It is another object of the invention to provide a biodegradable tampon applicator with at least one finger grip to aid the user during the insertion of the applicator in to the vaginal vault.

It is also another object of the invention to provide a biodegradable tampon applicator with improvements to reduce inconvenience and/or injury during insertion of the tampon into the vaginal vault.

It is another object of the invention to provide a film forming process to manufacture a biodegradable tampon applicator.

It is yet another object of the invention to provide a pin to be used in the film forming process to manufacture a tampon applicator.

It is another object of the invention to provide a tampon applicator with at least one indicium thereon.

Further and other objects of the invention will become apparent to those skilled in the art from the following summary of the invention, figures, detailed descriptions of the invention, examples and appended claims.

SUMMARY OF THE INVENTION

According to one aspect of the invention, there is provided a first pin having a predetermined length, to form a plunger of a tampon applicator, and a second pin having a predetermined length, to form a barrel of a tampon applicator. The first pin has a first end and a second end, said second end being a predetermined distance from said first end. The first pin is substantially column shaped. Said second end of said first pin being substantially dome shaped. Along said first pin, adjacent said dome is a peripheral depression ring. Said first pin having a diameter commencing at said first end and terminating at said second end, wherein said diameter of said first pin tapers downward from said first end to said second end. The second pin has a first end and a second end, said second end being a predetermined distance from said first end. The second pin is substantially column shaped. Said second pin has a diameter commencing at said first end and terminating at said second end, wherein said diameter of said second pin tapers downward from said first end to said second end. Said second end of said second pin is substantially dome shaped. Proximate said first end of said second pin is a peripheral depression ring. Said second pin further comprises a peripheral flange proximate said first end and adjacent said depression ring. The diameter of said second pin is greater than the diameter of said first pin. Each of said pins are used in a film forming process to form a tampon applicator. In a preferred embodiment, at least one of said pins further comprises at least one indicium such that said indicium will be transposed onto at least one of said barrel or plunger. Preferably said indicium comprises a marketing message, logo, health message or the like.

Said plunger and barrel being formed by exposing said first and second pin respectively to a composition that forms a film on each of said pins, such that the plunger and barrel formed therefrom will exhibit properties suitable to allow the plunger and barrel to operate together as a tampon applicator that is substantially biodegradable and substantially water soluble.

In one aspect of the invention, the pins are preferably dipped into a composition comprising at least one compound selected from the group consisting of substantially biodegradable, substantially water soluble film forming compound, cellulose ether, hydrocolloid, sequestering agent, hydroxypropylmethyl cellulose, starch, pullulan, film former, and Polyvinyl Alcohol. The composition may further comprise at least one additive to assist in the film forming process, a plasticizer, a gelatinizing agent, carrageenan, gellan gum and other additives. Suitable compositions for the tampon applicator of this invention may be found in U.S. Pat. Nos. 2,526,683, 5,264,223, 5,432,917 and US2010/0168410 herein incorporated by reference. The compositions therein have been used to manufacture oral capsules but have not been used to manufacture tampon applicators. Preferably, in one embodiment, the composition is comprised of from about 90 to about 99.98% by weight of a cellulose ether or mixture of cellulose ethers with water content of about 2 to about 10%, from about 0.01 to about 5% by weight of a hydrocolloid or mixtures of hydrocolloids, and from about 0.01 to about 5% by weight of a sequestering agent or agents. In another embodiment, the composition is preferably from about 5 to about 25 parts by weight of a water-soluble cellulose derivative, from about 0.1 to about 0.5 parts by weight of a gelatinizing agent and from about 0.01 to about 0.5 parts by weight of an auxiliary for gelation. The pins are dipped into the composition for a predetermined period of time to allow the composition to form a film on each of said pins. Preferably each pin is substantially lubricated prior to being dipped into the composition, to assist in the removal of the film from said pin after dipping into the composition. Suitable lubricants include, but are not limited to, Lecithin & Lecithin/mineral oil. Once the pins have been dipped into the composition, the pins are removed from the composition and the composition is allowed to dry on the pins until the moisture content of the film is in a suitable range, preferably about 3-7%. The thickness of said film is preferably in the range of about 1.5 to 3 millimeters. In another embodiment of the invention, the pins are sprayed with the composition. Film forming technology can be found in U.S. Pat. Nos. 2,526,683, 5,264,223, 5,431,917 and US 2010/0168410 which relate to film forming technologies for capsules used in the pharmaceutical industry, herein incorporated by reference. Once the film has dried to the desirable moisture level, the film is stripped from each of the pins into a cylindrical tube, preferably a collet, wherein the ends opposite the domed ends are cut to a precise finish. The plunger dome end is cut to ensure the string portion of the pledget is pushed through the plunger and out the second end. Preferably said cut is in the range of 2-10 millimeters.

The barrel dome end is cut, to allow the pledget to be pushed through the barrel and into the vaginal vault without substantial obstruction, whilst maintaining said pledget in said barrel during packaging, transportation and during the act of inserting the pledget into the vaginal vault. In one embodiment, said cut is in the range of 5-13 millimeters, in another embodiment, said cut is a series of petal like cuts, wherein a cut is made along the dome of the barrel and at least one more cut is made at preferably 90 degrees to said first cut, forming a petal like cut, preferably said cut is 5-15 millimeters in depth. Regardless of the cut made, the cuts are preferably smooth to avoid issues during insertion in to the vaginal vault, and allow the pledget to be inserted into the vaginal vault.

According to yet another aspect of the invention, there is provided a tampon applicator comprising a plunger and a barrel, preferably made by film forming technology, even more preferably using the pins described herein. Said plunger and barrel being made of a composition that is substantially biodegradable and substantially water soluble, preferably being made of a composition described herein. Said plunger being of a predetermined length, and having a first end and a second end. Said second end being a predetermined distance from said first end. Said plunger being substantially cylindrical in shape and having a first diameter at said first end and a second diameter at said second end, wherein said first diameter tapers downwards to said second diameter. Proximate said first end, said plunger further comprises a first mating portion, preferably a peripheral depression ring. Said barrel having a first end and a second end. Said second end being a predetermined distance from said first end. Said barrel being substantially cylindrical in shape and having a diameter greater than the first diameter of said plunger, to allow for a substantially "snug" fit of the plunger into said barrel whilst preventing the plunger from extending beyond the end of said barrel and entering the vaginal vault. Proximate said first end of said barrel, there is provided a second mating portion to matingly engage said first mating portion of said plunger to maintain said plunger in relation to said barrel in a first position, and to prevent the plunger from separating from said barrel during packaging, handling and shipping. Preferably said second mating portion is a peripheral depression ring, to matingly engage the peripheral depression ring of said plunger. Proximate said first end of said barrel, adjacent said second mating portion, said barrel further comprises a finger-grip area to assist a user in gripping the barrel of the tampon applicator whilst pushing the plunger into the barrel causing the tampon to be inserted into the vaginal vault. In a preferred embodiment, the fingergrip area is substantially flange like.

In a preferred embodiment, said tampon applicator further comprises at least one indicium. Preferably, said at least one indicium comprises a marketing message, logo, health message or the like. Preferably, said at least one indicium is formed during the film forming process of said barrel or plunger. Preferably, said at least one indicium is situated on at least one of said barrel or plunger, or both, preferably as a depression or as an elevation. In yet another embodiment, said indicium on each of said barrel and plunger, further acts as a locking mechanism to prevent the plunger from entering the vaginal vault.

According to another aspect of the invention, said tampon applicator exhibits water dispersible qualities within a predetermined time period that will not have a substantially negative effect on the environment, home septic systems, toilets, and waste water treatment plants. Preferably the tampon applicator of the present invention is substantially dissolvable in water having a temperature range of between about 5-40 C, preferably ambient temperature, within about two hours from exposure to said water. Preferably, said within about two hours is based on a USP dissolution test discussed herein. The USP dissolution test simulates the tampon applicator once flushed in a toilet and moves continuously as it makes its way to a sewage treatment plant.

BRIEF DESCRIPTION OF THE DRAWINGS

The following figures illustrate preferred and alternative embodiments of the invention, wherein.

DETAILED DESCRIPTION OF THE INVENTION

Referring now to FIGS. 1, 2, 3 and 4, the plunger pin 10, has a locking ring 20 near the dome 30 as an indentation. The locking ring 20, is preferably strong enough to hold the plunger 50 inside the barrel 60, and to allow the consumer to push the plunger 50 into the barrel 60 thus allowing the cotton tampon or pledget (not shown) to be pushed through the barrel 60 and into the vaginal vault.

Figure 1:
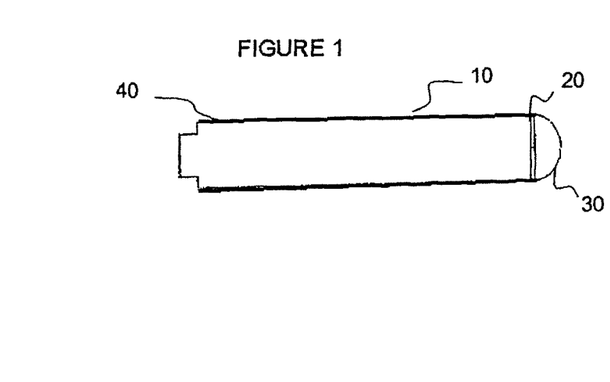
FIG. 1 is a side view of a preferred embodiment of the pin for the plunger element of the tampon applicator according to the present invention.
Figures 3, 4:
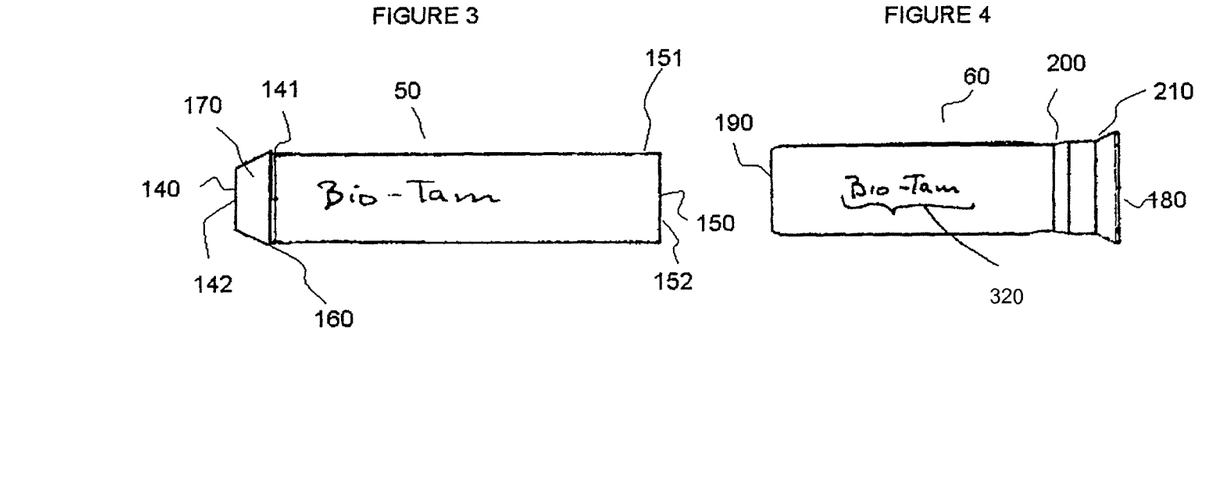
FIG. 3 is a side view of the plunger formed by the pin of FIG. 1 according to the present invention.
FIG. 4 is a side view of the barrel formed by the pin of FIG. 2 according to the present invention.
Figure 5A:
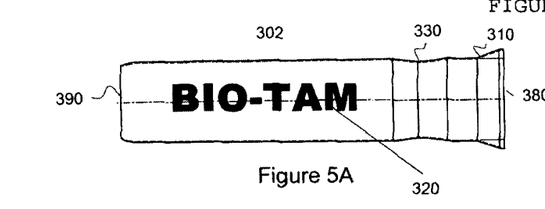
FIG. 5 is the tampon applicator of FIGS. 3 and 4 at various stages, according to the present invention.
Figure 5B:
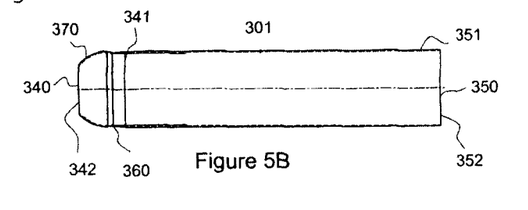
Figure 5C:
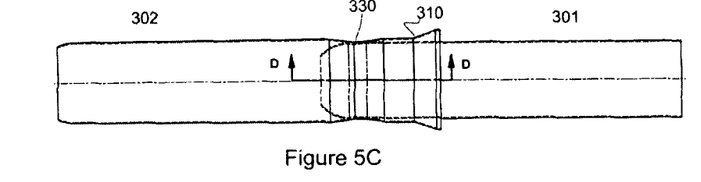
Figure 5D:
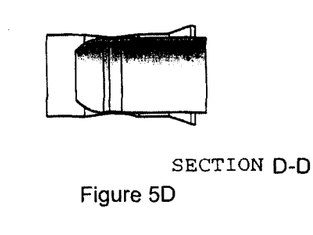
Figure 5E:
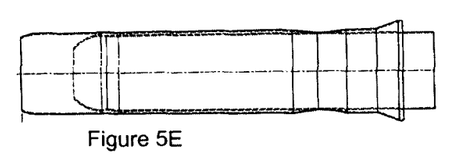
Figure 5F:
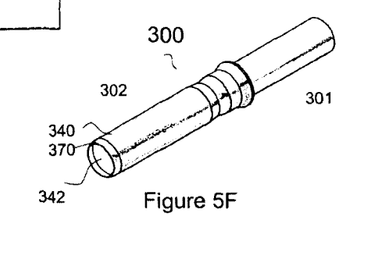
Figure 6A:
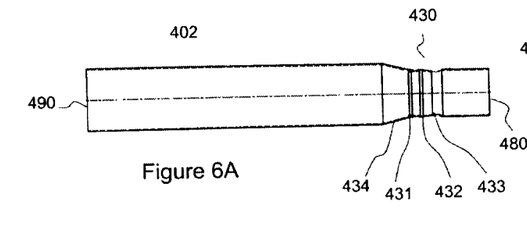
FIG. 6 is the tampon applicator in another embodiment of the present invention at various stages, according to the present invention.
Figure 6B:
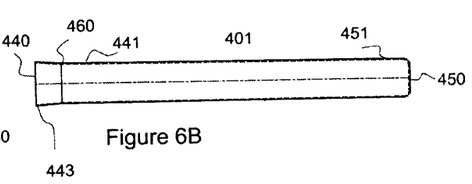
Figure 6C:
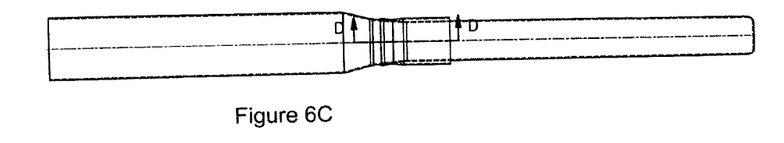
Figure 6D:
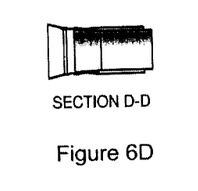
Figure 6E:
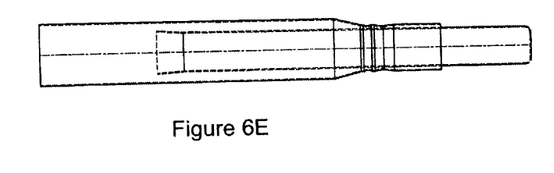
Figure 6F:
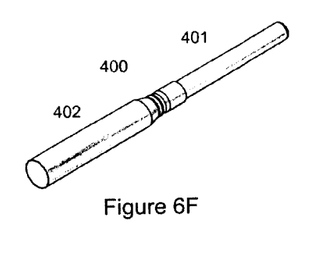

The plunger pin 10 is slightly tapered from the dome 30 (smaller diameter) to the end 40 away from the dome (larger diameter). This taper is meant to ensure a "snug" fit of the plunger 50 into the barrel 60 and prevent the plunger 50 from being pushed through the barrel 60. This will prevent issues on insertion and it will prevent the plunger 50 from entering the vaginal vault.

Figure 2:
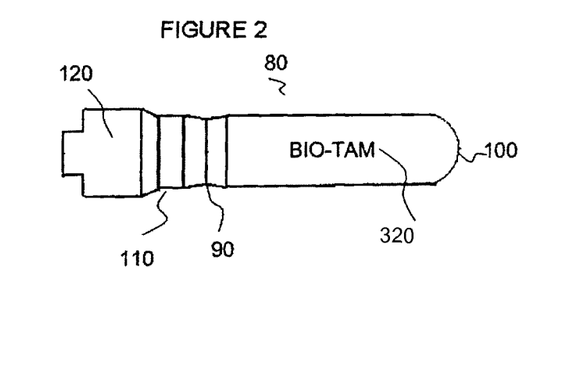
FIG. 2 is a side view of a preferred embodiment of the pin for the barrel element of the tampon applicator according to the present applicator.

The barrel pin 80 of the tampon applicator has several features:

The barrel pin locking ring 90 appears near the end of the barrel farthest away from the barrel pin dome 100. In order to create the barrel pin locking ring 90, a "V" or "U" shaped indentation is designed to create a ring around the entire barrel 60 when the barrel pin 80 is dipped in the molten raw materials chosen based on the desired composition.

In order to create the "finger-tip grip" 110 the barrel pin 80 flares out, preferably at a 20 degree angle then flatten back out towards the end 120 opposite the dome end 100. This creates an outward flange that will serve as the finger tip grip 110. The barrel pin 80 further comprises an indicium 320 located thereon. The indicium 320 is either depressed or raised along the body thereof. Similarly, the plunger pin 10 may also have an indicium situated thereon (not shown). If both the barrel pin 80 and plunger pin 10 each have an indicium thereon, the resulting indicium on the barrel 60 and plunger 80 will act not only as an indicium for marketing message, logo, health message or the like, but also as a locking mechanism to prevent the plunger 80 from entering the vaginal vault.

The following is a detailed description of a preferred embodiment of the barrel and plunger of the tampon applicator.

Barrel & Plunger Assembly, Referring Now to FIG. 5,

The tampon applicator 300 comprises a plunger 301 and a barrel 302. Said plunger 301 and barrel 302 being made of a material that is substantially biodegradable and substantially water soluble. Said plunger 301 being of a predetermined length, and having a first end 340 and a second end 350. Said second end 350 being a predetermined distance from said first end 340. Said plunger 301 being substantially cylindrical in shape and having a first diameter 341 at said first end 340 and a second diameter 351 at said second end 350, wherein said first diameter 341 tapers downwards to said second diameter 351. Said plunger 301 being hollow from said first end 340 to said second end 350, thus having a first opening 342 and a second opening 352. Proximate said first end 340, said plunger 301 further comprises a first mating portion 360, preferably in the shape of an indentation ring. Proximate the first end 340 and adjacent said first mating portion 360, said first opening 342 of said plunger 301 is formed as a truncated dome 370.

Said barrel 302 having a first end 380 and a second end 390. Said second end 390 being at a predetermined distance from said first end 380. Said barrel 302 being substantially cylindrical in shape and having a diameter greater than the first diameter 341 of said plunger 301, to allow for a substantially "snug" fit of the plunger 301 into said barrel 302 whilst preventing the plunger 301 from extending beyond the second end 390 of said barrel 302 and entering the vaginal vault.

In a preferred embodiment, the barrel 302 is hollow from said first end 380 to said second end 390. Said barrel 302 is hollow to allow a pledget to be inserted therein. Proximate said first end 380 of said barrel 302, there is provided a second mating portion 330 in the shape of a locking ring, to matingly engage said first mating portion 360 of said plunger 301 to maintain said plunger 301 in relation to said barrel 302 in a first position (see FIG. 5C), and to prevent the plunger 301 from separating from said barrel 302 during packaging, handling and shipping. Proximate said first end 380 of said barrel 302, adjacent said second mating portion 330, said barrel 302 further comprises a fingergrip area 310 to assist in gripping the barrel 302 of the tampon applicator 300 whilst pushing the plunger 301 into the barrel 302 causing the tampon or pledget to be inserted into the vaginal vault. The fingergrip area 310 is substantially flange like.

In a preferred embodiment, said tampon applicator further comprises at least one indicium 320. Preferable said at least one indicium 320 comprises a marketing message or logo or the like. Preferably said at least one indicium 320 is formed during the film forming process of said barrel 302 or plunger 301. Referring now to FIG. 3, the plunger is shown with an indicium 320 thereon. Referring now to FIG. 4, the barrel is shown with an indicium 320 thereon. When the indentation ring 360 of the plunger 301 is inserted into the barrel 302, it will slide until it "locks" within the "V" or "U" groove of the barrel locking ring 330. When the rings of both the barrel and plunger are aligned correctly, there will be a "snug" fit and the barrel and plunger will be secured to each other in a first position (see FIG. 5D). The rings 330 and 360 act to hold the plunger and barrel together, for shipping and transportation. However, once in the hands of a consumer, pressure exerted on the end 350 of the plunger 301, the consumer will be able to push the plunger 301 into the barrel 302 to extract the cotton tampon or pledget into the vaginal vault (see FIG. 5E).

Other embodiments of the barrel and plunger configuration are depicted in FIGS. 6-10.

In one embodiment illustrated in FIG. 6, the rim 440 of the plunger 401 is tapered outwardly having a diameter 443 greater than the diameter 441. In this embodiment the barrel 402 has an embossed ring 432 bordered by indented rings 431 and 433 at the mating area 430. This way there is no need to create an embossed ring on the plunger 401 since its mating function is fulfilled by the means of the rim 440 with diameter 443. Preferably, during the manufacturing process of the tampon applicator 400, the plunger 401 is inserted into the barrel 402 from the end 490 while the end 450 is inserted first till the rim 440 locks into the ring 432 (see FIGS. 6C and 6D). This assists in retrieval of the tampon applicator 400 from the vaginal chamber following the insertion of the tampon by pulling the assembly by the end 450 while avoiding the possibility of leaving the barrel 402 inside the vaginal chamber.

Figures 7A, 7B, 7C, 7D, 7E, 7F:
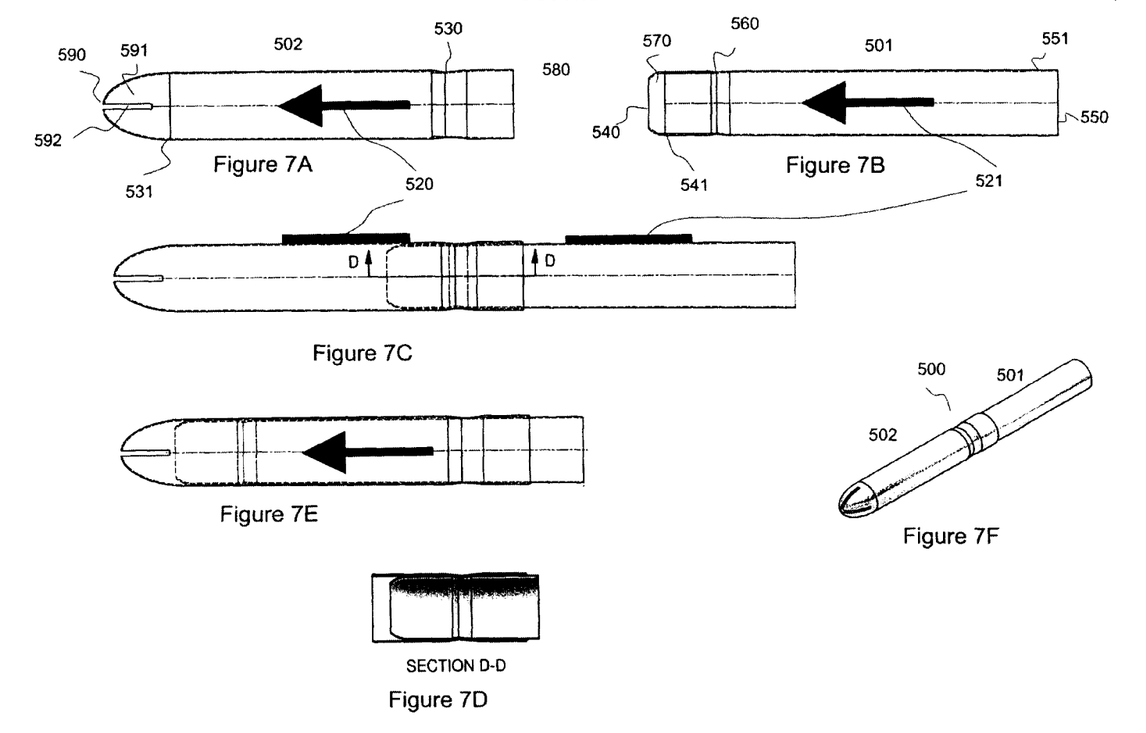
FIG. 7 is the tampon applicator in another embodiment of the present invention at various stages, according to the present invention.
Figure 8A:
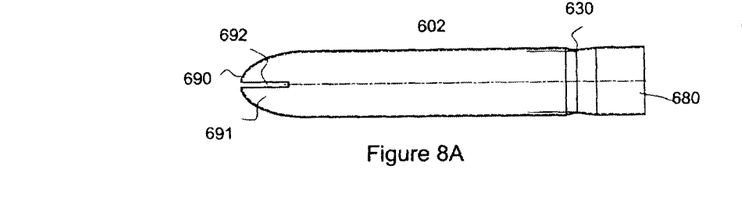
FIG. 8 is the tampon applicator in another embodiment of the present invention at various stages, according to the present invention.
Figure 8B:
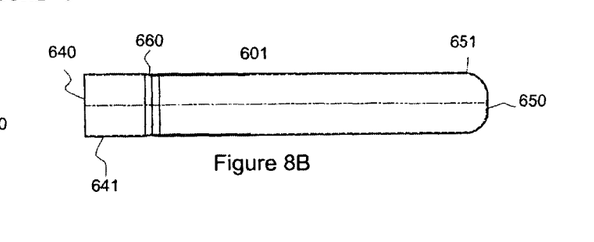
Figure 8C:
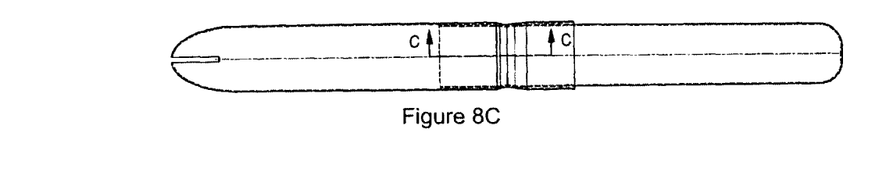
Figures 8D, 8E:
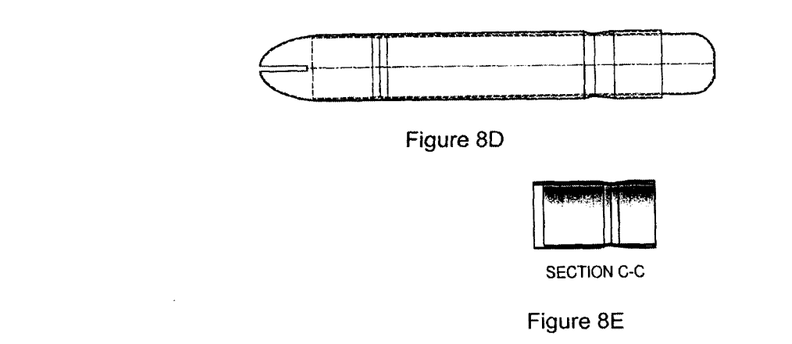
Figure 8F:
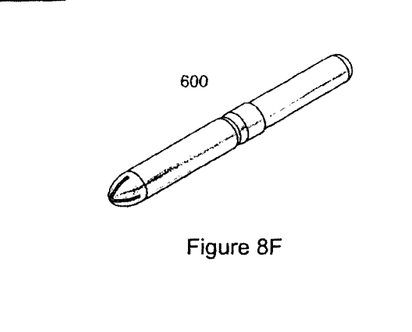

In another embodiment illustrated in FIG. 7, the first end 590 of the barrel 502 has a number of petals 591 separated by cuts 592. Petals 591 facilitate the insertion of the tampon applicator 500 into the vaginal chamber as well as assisting in the delivery of the tampon or pledget. The pressure of the plunger 501 on the tampon (not illustrated) causes opening of the petals and release of the tampon into the chamber. In this embodiment the plunger 501 comprises a depressed ring 560 to mate with a depressed ring 530 of the barrel 502 to maintain the tampon applicator 500 together during shipping (see FIG. 7C). In this embodiment the diameter 551 is greater than the diameter 541 and smaller than the diameter 531, to prevent extension of the plunger 501 from the end 590 of the barrel 502 (see FIG. 7E).

Indicium 520 shown on barrel 502 is raised. Similarly, indicium 521 shown on plunger 501 is raised (see FIG. 7C depicting the plunger and a barrel from the side view). In this embodiment, the indicia 520 and 521 when the plunger 501 is inserted into the barrel 502, will matingly engage with each other to further act as a locking mechanism to prevent extension of the plunger 501 from entering the vaginal vault, once the tampon has been inserted (see FIG. 7E). In this instance, indicium 520 will be slightly larger than indicium 521 to allow for matingly engagement.

The barrel and the plunger each may have more than one indicium, either substantially identical to each other, matingly completing each other, such that one indicium matingly engages with the other indicium, or having an aesthetical feature.

In yet another embodiment illustrated in FIG. 8, the barrel 602 has a tapered end 690 equipped with substantially flexible petals 631 facilitating insertion of the tampon applicator 600 into the vaginal chamber. The number of petals may vary, but preferably may be 3, 4 or more, depending on the manufacturing preferences and material selection. Further in this embodiment the second end 650 of the plunger 601 is closed and dome-shaped thus creating an air pressure in addition to a mechanical pressure during the extraction of the tampon from the barrel 602 into the vagina chamber. Further in this embodiment the diameter 651 at the end 650 is smaller than the diameter 641 at the end 640.

Figure 9A:
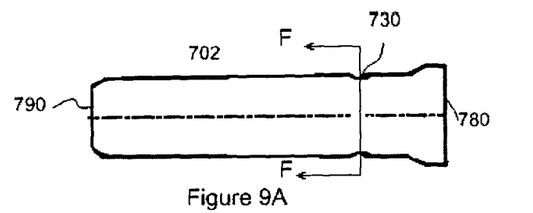
FIG. 9 is the tampon applicator in another embodiment of the present invention, according to the present invention.
Figure 9B:
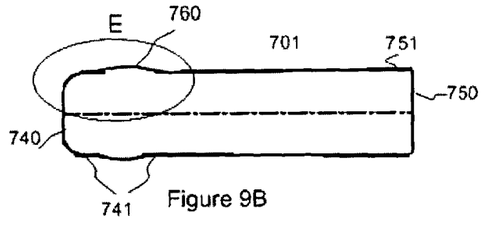
Figure 9C:
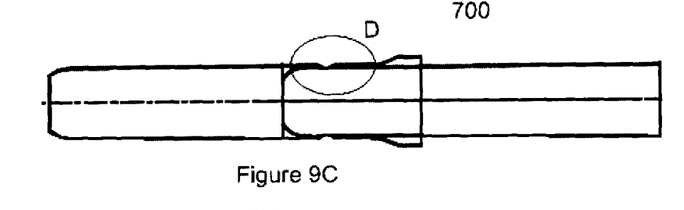
Figure 9D:
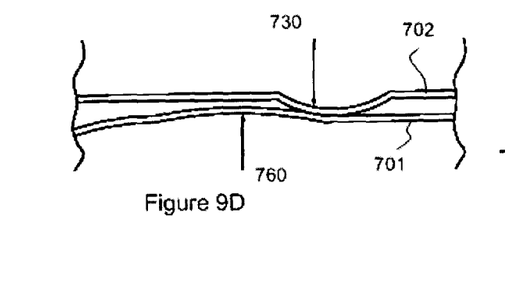
Figures 9E, 9F:
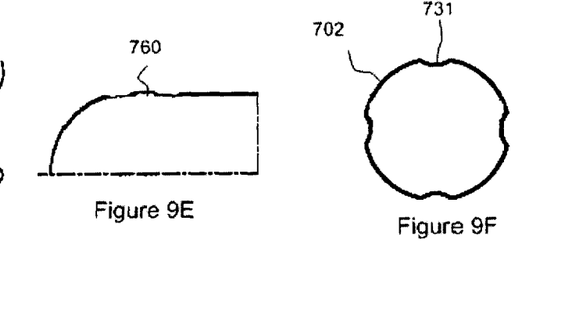

In still another embodiment illustrated in FIG. 9, the mating member 760 of the plunger 701 is raised and not depressed (see FIG. 9E). Thus the diameter 760 is larger than the diameter 741 while smaller than the diameter 751. Further, the mating member 730 of the barrel 702, in this embodiment, is a plurality of recesses 731, best illustrated in FIG. 9F. The mating of the plunger 701 and the barrel 702 is best illustrated in FIG. 9D. The number of recesses may vary but preferably can be 2, 3, 4 or more and the form of those recesses 731 can be rounded, triangular or irregular as per manufacturing preferences.

Figures 10, 10A:
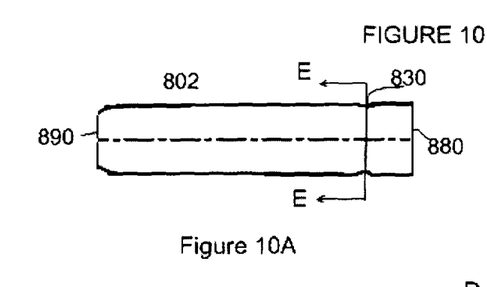
FIG. 10 is the tampon applicator in another embodiment of the present invention, according to the present invention.
Figure 10B:
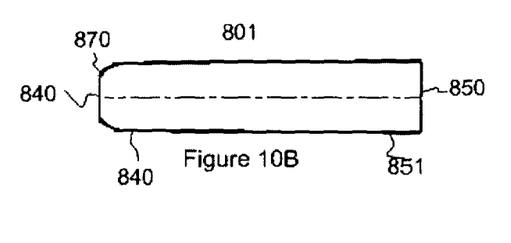
Figures 10C, 10D, 10E:
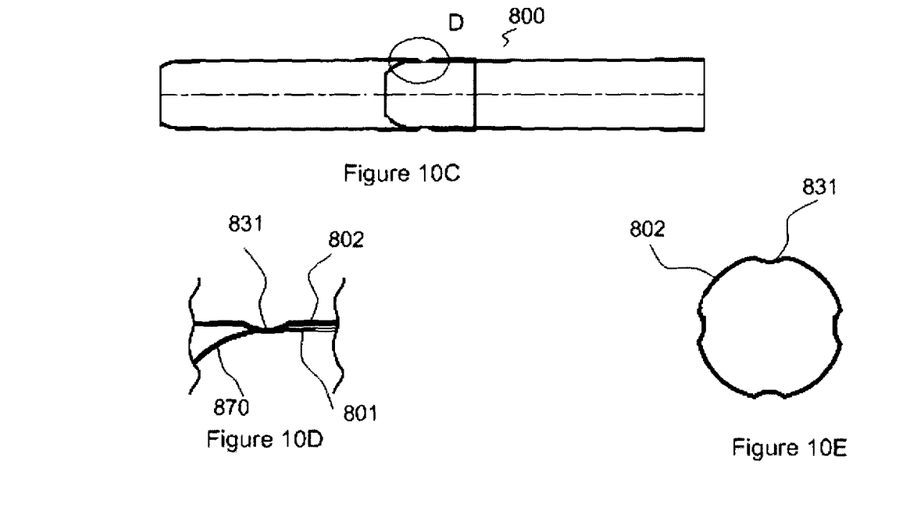

The embodiment illustrated in FIG. 10 is similar to the one at FIG. 9, the main difference is that the mating member 830 of the barrel 802 grips the outer wall of the plunger 801 (see FIG. 10D) with recesses 831.

All the features illustrated in the provided figures are exemplary and can be interchanged between the embodiments without departing from the scope of the invention. For example the embodiments in FIG. 9 of 10 may have same leaflets as in the FIG. 8 and so on.

Dissolution Study.

The following is a detailed description of a preferred embodiment of the tampon applicator undergoing a dissolution study.

Two different methods were used to determine disintegration:

1. Using a USP DT (Disintegration Test) Apparatus at 25 C

The DT apparatus consists of a basket, rack assembly and a mechanical device to move it up and down. A rigid basket-rack assembly supporting three cylindrical glass tubes about 106 mm long, about 32.5 mm in internal diameter and about 3 mm thick, attached to a mechanical device, which in turn raised and lowered the basket smoothly at a constant frequency of between 28 and 32 cycles per minute through a distance of 50 to 60 mm. The tampon applicator was inserted in to the basket and the dissolution test was conducted. Results are depicted below.

2. Disintegration Test Using Magnetic Stirrer Method

This test incorporated a 100 ml glass beaker, magnetic stirrer and magnetic stirrer unit, thermometer, stopwatch, tampon applicator and distilled water.

800 ml of distilled water was placed in the beaker and the temperature of the water was maintained at 25+/−1° C. The magnetic stirrer was placed in the beaker. The magnetic stirrer unit was turned on and the speed was set in order to have a water vortex of 25+/−5 mm (1"+/−¼"). The tampon applicator was placed in the beaker and simultaneously the stopwatch was switched on until 90% of the tampon applicator was dissolved. Thereupon the stopwatch was switched off. On average, 90% of the tampon applicator was dissolved between about 38 to about 43 minutes. The remaining 10% dissolved within about 120 minutes from initiating each study.

| Comparison of DT time | | |
|---|---|---|
| | DT time (minutes:seconds) | |
| Sample No. | Magnetic stirrer method | USP apparatus |
| 1 | 46:18 | 37:41 |
| 2 | 50:14 | 38:33 |
| 3 | 43:42 | 38:55 |
| Average | 46:44 | 38:23 |

The following is a detailed description of a preferred embodiment of the dipping process used to manufacture the tampon applicator of the present invention.

The stainless steel pins are dipped into the solution and slowly withdrawn to ensure an even distribution of the raw material. The depth of the dip will be in the range of 4-6 mm from the eventual cut line of the applicator.

The pins are then flipped 360 degrees in a circular manner to further ensure even distribution of the film.

With the dome of the pins facing upwards, the pins will now go through a drying phase where the removal of moisture from the film is enhanced by the addition of warm dry air.

The timing of this process is in the range of about 30-60 minutes and the moisture level in the film is in the range of 3-7%.

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

What is claimed is:

1. A substantially biodegradable and water soluble tampon applicator comprising:
   a plunger and a barrel, said plunger being of a predetermined length, and having a first end and a second end, said second end being a predetermined distance from said first end, said plunger being substantially cylindrical in shape and having a first diameter at said first end and a second diameter at said second end, wherein said first diameter tapers downwards to said second diameter, proximate said first end, said plunger further comprises a first mating portion, said barrel having a first end and a second end, said second end being a predetermined distance from said first end, said barrel being substantially cylindrical in shape and having a diameter greater than the first diameter of said plunger, second mating portion proximate said first end of said barrel is provided to matingly engage said first mating portion of said plunger to maintain said plunger in relation to said barrel in a first position, said barrel further comprises a fingergrip proximate said first end of said barrel and adjacent said second mating portion;

wherein said plunger and said barrel comprise a film having a moisture content of about 2-8% and a thickness in the range of about 1.5 to 3 millimeters.

2. The tampon applicator of claim 1 further comprising at least one indicium.

3. The tampon applicator of claim 2 wherein the at least one indicium is selected from the group consisting of a marketing message, logo, and health message.

4. The tampon applicator of claim 3, wherein said indicium further acts as a locking mechanism.

5. The tampon applicator of claim 2, wherein said indicium further acts as a locking mechanism.

6. The tampon applicator of claim 1, wherein said tampon applicator substantially dissolves in water.

7. The tampon applicator of claim 6 wherein said tampon applicator substantially commences dissolution in water in less than about 10 minutes and substantially dissolve to about 10% of its original mass within the first hour.

8. A substantially biodegradable and water soluble tampon applicator comprising:

a plunger and a barrel, said plunger being of a predetermined length, and having a first end and a second end, said second end being a predetermined distance from said first end, said plunger being substantially cylindrical in shape and having a first diameter at said first end and a second diameter at said second end, wherein said first diameter tapers downwards to said second diameter, proximate said first end, said plunger further comprises a first mating portion, said barrel having a first end and a second end, said second end being a predetermined distance from said first end, said barrel being substantially cylindrical in shape and having a diameter greater than the first diameter of said plunger, a second mating portion proximate said first end of said barrel is provided to matingly engage said first mating portion of said plunger to maintain said plunger in relation to said barrel in a first position, said barrel further comprises a fingergrip proximate said first end of said barrel and adjacent said second mating portion;

wherein said plunger and said barrel are made from a composition of from about 90 to about 99.89% by weight of a cellulose ether or mixture of cellulose ethers with water content of about 2 to about 10%, from about 0.01 to about 5% by weight of a hydrocolloid or mixtures of hydrocolloids, and from about 0.01 to about 5% by weight of a sequestering agent or agents.

9. The tampon applicator of claim 8 further comprising at least one indicium.

10. The tampon applicator of claim 9, wherein said indicium further acts as a locking mechanism.

11. The tampon applicator of claim 8, wherein said tampon applicator substantially dissolves in water.

12. A substantially biodegradable and water soluble tampon applicator comprising:

a plunger and a barrel, said plunger being of a predetermined length, and having a first end and a second end, said second end being a predetermined distance from said first end, said plunger being substantially cylindrical in shape and having a first diameter at said first end and a second diameter at said second end, wherein said first diameter tapers downwards to said second diameter, proximate said first end, said plunger further comprises a first mating portion, said barrel having a first end and a second end, said second end being a predetermined distance from said first end, said barrel being substantially cylindrical in shape and having a diameter greater than the first diameter of said plunger, a second mating portion proximate said first end of said barrel is provided to matingly engage said first mating portion of said plunger to maintain said plunger in relation to said barrel in a first position, said barrel further comprises a fingergrip proximate said first end of said barrel and adjacent said second mating portion;

wherein said plunger and said barrel are made from a composition of from about 5 to about 25 parts by weight of a water-soluble cellulose derivative, from about 0.1 to about 0.5 parts by weight of a gelatinizing agent, and from about 0.01 to about 0.5 parts by weight of an auxiliary for gelation.

13. The tampon applicator of claim 12 further comprising at least one indicium.

14. The tampon applicator of claim 13, wherein said indicium further acts as a locking mechanism.

15. The tampon applicator of claim 12, wherein said tampon applicator substantially dissolves in water.

16. A substantially biodegradable and water soluble tampon applicator comprising:

a plunger and a barrel, said plunger being of a predetermined length, and having a first end and a second end, said second end being a predetermined distance from said first end, said plunger being substantially cylindrical in shape and having a first diameter at said first end and a second diameter at said second end, wherein said first diameter tapers downwards to said second diameter, proximate said first end, said plunger further comprises a first mating portion, said barrel having a first end and a second end, said second end being a predetermined distance from said first end, said barrel being substantially cylindrical in shape and having a diameter greater than the first diameter of said plunger, a second mating portion proximate said first end of said barrel is provided to matingly engage said first mating portion of said plunger to maintain said plunger in relation to said barrel in a first position, said barrel further comprises a fingergrip proximate said first end of said barrel and adjacent said second mating portion;

wherein said plunger and said barrel have a composition comprising hydroxypropylmethyl cellulose, starch, pullulan and polyvinyl alcohol.

17. The tampon applicator of claim 16 further comprising at least one indicium.

18. The tampon applicator of claim 17, wherein said indicium further acts as a locking mechanism.

19. The tampon applicator of claim 16, wherein said tampon applicator substantially dissolves in water.

* * * * *